United States Patent [19]

Choi et al.

[11] Patent Number: 5,705,640

[45] Date of Patent: Jan. 6, 1998

[54] O-CARBAMOYL-(D)-PHENYLALANINOL COMPOUNDS, THEIR PHARMACEUTICALLY USEFUL SALTS AND PROCESS FOR PREPARING THE SAME

[75] Inventors: Yong Moon Choi, Towaco, N.J.; Dong Il Han; Yong Kil Kim, both of Taejon, Rep. of Korea

[73] Assignee: Yukong Limited, Seoul, Rep. of Korea

[21] Appl. No.: 596,496

[22] Filed: Feb. 5, 1996

[30] Foreign Application Priority Data

Feb. 11, 1995 [KR]  Rep. of Korea ............. 1995-2543

[51] Int. Cl.$^6$ ............................................. C07D 265/30
[52] U.S. Cl. ..................... 544/169; 544/389; 546/226; 548/531; 560/115; 560/163
[58] Field of Search ......................... 560/163, 115; 548/531; 546/226; 544/169, 385

*Primary Examiner*—Michael L. Shippen
*Attorney, Agent, or Firm*—Abelman, Frayne & Schwab

[57] ABSTRACT

The present invention relates to O-carbamoyl-(D)-phenylalaninol compound represented by the following structural formula V and pharmaceutically acceptable salts thereof to treat diseases of the central nervous system:

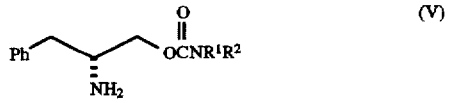

wherein $R^1$ and $R^2$ may be the same with or different from each other and are independently selected from the group consisting of hydrogen, lower alkyl containing 1 to 8 carbon atoms, and 5 to 7-membered aliphatic cyclic compounds which may comprise not more than two nitrogen or oxygen atoms directly unconnected, the total number of carbon atom of $R^1$ and $R^2$ ranging from 0 to 16.

2 Claims, No Drawings

O-CARBAMOYL-(D)-PHENYLALANINOL COMPOUNDS, THEIR PHARMACEUTICALLY USEFUL SALTS AND PROCESS FOR PREPARING THE SAME

BACKGROUND OF THE INVENTION

1. Field of the Invention

The present invention relates, in general, to novel stereospecific phenylalkylamino carbamate compounds and pharmaceutically useful salts thereof, useful to treat the diseases of the central nervous system. More particularly, the present invention relates to O-carbamoyl-(D)-phenylalaninol compounds and pharmaceutically useful salts thereof. Also, the present invention is concerned with a process for preparing the same.

2. Description of the Prior Art

Phenylethylamine derivatives, one important class of therapeutical medicines useful for managing central nervous system (CNS) diseases, have been used mainly to treat obesity, narcolepsy, minimal brain dysfunction and mild depression.

Organic carbamates have been effectively used for controlling various CNS disorders. For example, J. Am. Chem. Soc., 73, 5779 (1951) discloses 2-methyl-2-propyl-1,3-propandiol dicarbamate and its pharmaceutical activity was verified in J. Pharmacol. Exp. Ther., 104, 229 (1952).

Besides, there are many carbamate compounds that are suggested as therapeutics for CNS disease in the prior arts. For example, U.S. Pat. Nos. 2,884,444 and 2,937,119 disclose carbamates, such as 2-phenyl-1,3-propandiol dicarbamate and isopropylmeprobamate, respectively. These compounds are found to be very effectively used as therapeutics for treating CNS disorders, especially as antiepileptic and centrally acting muscle relaxant. Research for the development of carbamate therapeutics for CNS diseases has been and continues to be actively advanced.

Recent design of pharmacologically useful compounds has been based on amino acids or the derivatives thereof, which is mainly attributable to the fact that many of the compounds found in biological systems come from amino acids or the derivatives thereof. In addition, in most cases, the function of a pharmaceutically useful compound is effected after it binds to an enzyme or receptor, which may trigger the regulatory mechanisms of the enzyme or receptor.

SUMMARY OF THE INVENTION

As a result of intensive and thorough research, the present inventors found that O-carbamoyl-(D)-phenylalaninol compounds are pharmaceutically useful for CNS disorders, especially for depression and anxiety.

Accordingly, it is a principal object of the present invention to provide novel O-carbamoyl-(D)-phenylalaninol carbamate compounds, represented by the following structural formula V:

wherein $R^1$ and $R^2$ may be the same with or different from each other and are independently selected from the group consisting of hydrogen, lower alkyl containing 1 to 8 carbon atoms, and 5 to 7-membered aliphatic cyclic compounds which may comprise not more than two nitrogen or oxygen atoms directly unconnected, the total number of carbon atom of $R^1$ and $R^2$ ranging from 0 to 16; and pharmaceutically acceptable salts thereof.

It is another object of the present invention to provide a process for preparing O-carbamoyl-(D)-phenylalaninols, represented by the above structural formula V.

DETAILED DESCRIPTION OF THE INVENTION

In accordance with the present invention, the O-carbamoyl-(D)-phenylalaninols represented by the structural formula V and pharmaceutically acceptable salts thereof can be prepared by the characteristic method comprising the steps of: reacting (D)-phenylalaninol represented by the following structural formula II:

with benzyl chloroformate in a basic aqueous solution to synthesize N-benzyloxycarbonyl-(D)-phenylalaninol, represented by the following structural formula III:

subjecting N-benzyloxycarbonyl-(D)-phenylalaninol of the structural formula III to carbamoylation with phosgene in the presence of an amine base, represented by the following general formula VI:

wherein $R^1$ and $R^2$ are the same as defined above, to produce O-carbamoyl-N-benzyloxycarbonyl-(D)-phenylalaninol, represented by the following structural formula IV:

wherein $R^1$ and $R^2$ are the same as defined above, deprotecting the benzyloxycarbonyl group from O-carbamoyl-N-benzyloxycarbonyl-(D)-phenylalaninol of the structural formula IV through hydrogenolysis in the presence of a catalyst, to afford O-carbamoyl-(D)-phenylalaninol compound, represented by the following structural formula V:

wherein $R^1$ and $R^2$ are the same as defined above; and treating O-carbamoyl-(D)-phenylalaninol compound of the structural formula V with an anhydrous acid, in an ethereal solution without further purification, to give a pharmaceutically acceptable salts thereof, represented by the following structural formula I:

wherein $R^1$ and $R^2$ are the same as defined above and HX is an acid capable of forming a pharmaceutically useful salt with the intramolecular basic nitrogen atom.

The compound of Structural Formula I is prepared as set forth in Reaction Scheme below.

REACTION SCHEME

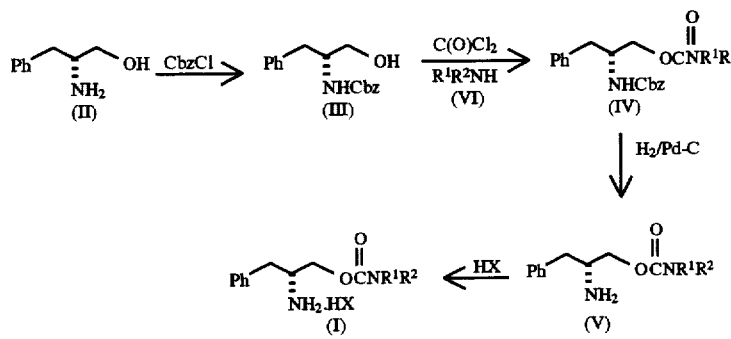

As shown in Reaction Scheme I, (D)-phenylalaninol (II) is first reacted with benzyl chloroformate in a basic aqueous solution, to give N-benzyloxycarbonyl-(D)-phenylalaninol (III) which is subjected to carbamoylation with phosgene in the presence of an amine base. Ammonolysis of the carbamoylated intermediate is carried out and an amine represented by the general formula VI is used to produce O-carbamoyl-N-benzyloxycarbonyl-(D)-phenylalaninol (IV) in a high yield within a short time. Removal of the benzyloxycarbonyl group, a nitrogen protecting group, from the O-carbamoyl-N-benzyloxycarbonyl-(D)-phenylalaninol (IV) through hydrogenolysis in the presence of a catalyst, affords O-carbamoyl-(D)-phenylalaninol (V) which is, then, treated with an anhydrous acid (HX) in an ether solution without further purification, to provide the salts (I) of O-carbamoyl-(D)-phenylalaninol. In Reaction Scheme, HX represents an acid suitable for the formation of pharmaceutically acceptable salts with the intramolecular basic nitrogen atom.

Details of the reaction conditions described in Reaction Scheme I are as follows. In the first step, the concentration of the starting material (II) is between 0.1 and 3 mole and benzyl chloroformate is used at 1 to 2 equivalents. The basic aqueous solution has a pH value between 7 and 14 and the conversion reaction is carried out at temperatures ranging from −10° to 70° C.

For the conversion of the compound (III) to the compound (IV), 1 to 2 molar equivalent of phosgene, either neat or as solution in toluene, is used at 0.01 to 2 molar concentration of the compound (III). Halogenated alkane such as methylene chloride, aromatic solvents such as toluene, or the mixtures thereof can be used as a solvent. Use of a base such as acid scavenger is recommended. Typically, a tertiary amine, such as triethylamine, diisopropylethylamine, triisopropylamine, DBU (1,6-diazabicyclo[5.4.0]undec-7-ene), DBN (1,5-diazabicyclo[4.3.0]non-5-ene), antipyrine and dimethylphenylamine, can be used for this purpose. The reacting amine can be used as neat or as solution in water or lower alkyl alcohol such as methanol, ethanol, n-propanol and isopropanol and 1 to 2 molar equivalent is used. The conversion reaction is carried out at temperatures ranging from −30° to 60° C.

As for the hydrogenation from the compound (IV) to the compound (V), an ethereal solvent such as THF, an alcoholic solvent such as methanol, water, an aromatic solvent such as toluene, benzene or xylene, an ester solvent such as ethyl acetate or any compositional mixture thereof is used as a reaction medium. The hydrogenation from the compound (IV) to the compound (V) is carried out at a temperature of −10° to 150° C. under a 1 to 100 atm hydrogen pressure. This reaction is performed in the presence of a catalyst, such as palladium, platinum, platinum oxide, rhodium, and iridium.

Concrete examples of the anhydrous acid used for the preparation of the compound (I) from the compound (V) include hydrochloric acid, sulfuric acid, phosphoric acid, acetic acid, benzoic acid, citric acid, malonic acid, salicylic acid, malic acid, fumaric acid, oxalic acid, succinic acid, tartaric acid, lactic acid, gluconic acid, ascorbic acid, maleic acid, aspartic acid, benzene sulfonic acid, methane sulfonic acid, ethane sulfonic acid, hydroxymethane sulfonic acid and hydroxyethane sulfonic acid and the like. Additional acids can refer to "Pharmaceutical Salts", J. Pharm. Sci., 1977; 66(1): 1–19. This preparation is executed in a reaction media which can be exemplified by an ethereal solvent such as THF, an alcoholic solvent such as methanol, an ester solvent such as ethyl acetate, an aromatic solvent, and any compositional mixture thereof. An ethereal solvent is recommended as an addition solution, including ethyl ether, propyl ether, isopropyl ether, butyl ether, isobutyl ether. The concentration of the compound (V) is on the order of 0.01 to 5 mole.

Representative examples of the compound (V) are suggested with structural formulas below:

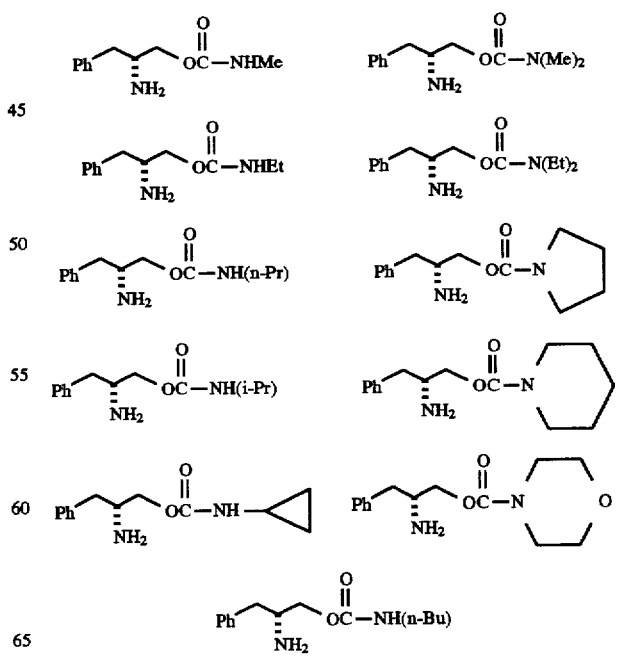

-continued

Ph-CH(NH₂)-CH₂-OC(=O)-N(piperazine)N-Ph

Ph-CH(NH₂)-CH₂-OC(=O)-NH(n-Oct)

Ph-CH(NH₂)-CH₂-OC(=O)-NH-cyclohexyl

For therapeutic use in medicines for treating pain, depression, anxiety, epilepsy, stroke, demential and Parkinson's disease, the compounds of the present invention, alone or in combination with pharmaceutically acceptable carrier, are administered to patients at a dosage of from 0.7 to 7,000 mg per day. For a normal human adult with a body weight of approximately 70 kg, the administration amount is translated into a daily dose of 0.01 to 100 mg per kg of body weight. The specific dosage employed, however, may vary depending upon the requirements of the patient, the severity of patient's condition and the activity of the compound. The determination of optimum dosages for a particular situation must clinically be done and is within the skill of the art.

In utilizing the compounds of the present invention for the central nervous system, particularly to treat depression, it is preferred to administer the compounds orally. Since the compounds absorb well orally, it usually will not be necessary to resort to parenteral administration. For oral administration, the compound (I) is preferably combined with a pharmaceutical carrier. The ratio of the carrier to the compound of Structural Formula (I) is not critical to express the effects of the medicine on the central nervous system, and they can vary considerably depending on whether the composition is to be filled into capsules or formed into tablets. In tableting, various edible pharmaceutical carriers or the mixture thereof can be used. A suitable carriers, for example, are a mixture of lactose, diabasic calcium phosphate and/or corn starch. Other pharmaceutically acceptable ingredients can be further added, including lubricants such as magnesium stearate.

Besides the compound of Structural Formula I, compositions comprising it are within the scope of the present invention. Furthermore, the present invention includes uses of the compound (I) and/or the composition.

A better understanding of the present invention may be obtained in light of following examples which are set forth to illustrate, but are not to be construed to limit, the present invention.

EXAMPLE I

O-(N-Methyl)-Carbamoyl-N-Benzyloxycarbonyl-D-Phenylalaninol

In a 250 mL flask, N-benzyloxycarbonyl-D-phenylalaninol (314 g, 0.011 mol) was dissolved in 150 ml of anhydrous THF under a nitrogen atmosphere and was added with antipyrine (2.27 g, 0.012 mol). The reaction mixture was cooled to 0° C. in an ice/water bath and phosgene (6.05 mL of 2M solution in toluene, 0.012 mol) was added at one try. After stirring for 1 hour, methylamine (0.38 g, 0.012 mol) was added. Following stirring at ambient temperatures for an extra 4 hours, water was added to terminate the reaction. The organic layer was extracted 3 times with dichloromethane, dried over magnesium sulfate and distilled in vacuo, to give a solid. This was recrystallized in a solution mixture of ethyl acetate and diethyl ether, to produce 2.93 g of O-(N-methyl)-carbamoyl-N-benzyloxycarbonyl-D-phenylalaninol: Yield 78%.

¹H-NMR(CDCl₃, 200 MHz), ppm(δ): 2.58–2.98(m,5H), 3.98–4.22(br,3H), 4.58–4.75(br,1H), 5.08(s,3H), 7.12–7.48 (m,10H).

EXAMPLE II

O-(N-Isopropyl)-Carbamoyl-N-Benzyloxycarbonyl-D-Phenylalaninol

The procedure given in Example I was followed using isopropyl amine as a reactant, instead of methyl amine, to give O-(N-isopropyl)-carbamoyl-N-benzyloxycarbonyl-D-phenylalaninol. A yield of 88% was obtained.

¹H-NMR(CDCl₃, 200 MHz), ppm(δ): 1.25(d,6H), 2.72–3.02(m,2H), 3.68–3.90(m,1H), 3.98–4.25(m,3H), 4.51–4.65(br,1H), 5.18(s,3H), 7.08–7.51(m,10H).

EXAMPLE III

O-(N-n-Octyl)-Carbamoyl-N-Benzyloxycarbonyl-D-phenylalaninol

The procedure given in Example I was followed using octyl amine as a reactant, instead of methyl amine, to give O-(N-n-octyl)-carbamoyl-N-benzyloxycarbonyl-D-phenylalaninol. A yield of 96% was obtained.

¹H-NMR(CDCl₃, 200 MHz), ppm(δ): 0.85(t,3H), 1.08–1.58(m,12H), 2.72–2.98(m,2H), 3.15(q,2H), 3.39–4.26 (m,3H), 3.39–4.26(m,3H), 4.65–4.78(br,1H), 5.10(s,3H), 7.08–7.48(m,10H).

EXAMPLE IV

O-(N-Cyclohexyl)-Carbamoyl-N-Benzyloxycarbonyl-D-phenylalaninol

The procedure given in Example I was followed using cyclohexyl amine as a reactant, instead of methyl amine, to give O-(N-cyclohexyl)-carbamoyl-N-benzyloxycarbonyl-D-phenylalaninol. A yield of 79% was obtained.

¹H-NMR(CDCl₃, 200 MHz), ppm(δ): 0.95–2.05(m,10H), 2.68–3.02(m,2H), 3.32–3.58(m,1H), 3.90–4.25(br,3H), 4.58–4.75(m,1H), 5.10(s,3H), 7.01–7.56(m,10H).

EXAMPLE V

O-(N,N'-Dimethyl)-Carbamoyl-N-Benzyloxycarbonyl-D-Phenylalaninol

The procedure given in Example I was followed using dimethyl amine as a reactant, instead of methyl amine, to give O-(N,N'-dimethyl)-carbamoyl-N-benzyloxycarbonyl-D-phenylalaninol. A yield of 94% was obtained.

¹H-NMR(CDCl₃, 200 MHz), ppm(δ): 2.55–3.05(br,6H), 3.85–4.28(m,3H), 4.90–5.48(m,4H), 6.80–7.70(m,10H).

EXAMPLE VI

O-(N-Pyrrolidyl)-Carbamoyl-N-Benzyloxycarbonyl-D-Phenylalaninol

The procedure given in Example I was followed using pyrrolidine as a reactant, instead of methyl amine, to give O-(N-pyrrolidyl)-carbamoyl-N-benzyloxycarbonyl-D-phenylalaninol. A yield of 80% was obtained.

$^1$H-NMR(CDCl$_3$, 200 MHz), ppm(δ): 1.85–2.05(br,4H), 2.82–3.18(m,2H), 3.18–3.48(m,4H), 3.92–4.28(m,3H), 5.08 (s,2H), 5.12–5.31(m,1H), 6.98–7.55(m,10H).

EXAMPLE VII

O-(N-Piperidyl)-Carbamoyl-N-Benzyloxycarbonyl-D-Phenylalaninol

The procedure given in Example I was followed using piperidine as a reactant, instead of methyl amine, to give O-(N-piperidyl)-carbamoyl-N-benzyloxycarbonyl-D-phenylalaninol. A yield of 80% was obtained.

$^1$H-NMR(CDCl$_3$, 200 MHz), ppm(δ): 1.35–1.85(br,6H), 2.72–3.05(m,2H), 3.32–3.58(m,4H), 3.95–4.38(m,3H), 5.05–5.28(m,3H), 7.05–7.52(m,10H).

EXAMPLE VIII

O-(N-Morpholino)-Carbamoyl-N-Benzyloxycarbonyl-D-Phenylalaninol

The procedure given in Example I was followed using morpholine as a reactant, instead of methyl amine, to give O-(N-morpholino)-carbamoyl-N-benzyloxycarbonyl-D-phenylalaninol. A yield of 85% was obtained.

$^1$H-NMR(CDCl$_3$, 200 MHz), ppm(δ): 2.72–3.02(m,2H), 3.25–3.55(br,4H), 3.55–3.80(br,4H), 3.95–4.30(m,3H), 5.15 (s,3H), 7.05–7.51(m,10H),

EXAMPLE IX

O-[N-(N-Phenyl)piperazino]-Carbamoyl-N-Benzyloxycarbonyl-D-Phenylalaninol

The procedure given in Example I was followed using N-phenylpiperazine as a reactant, instead of methyl amine, to give O-[N-(N-phenyl)piperazino]-carbamoyl-N-benzyloxycarbonyl-D-phenylalaninol. A yield of 93% was obtained.

$^1$H-NMR(CDCl$_3$, 200 MHz), ppm(δ): 2.72–3.02(m,2H), 3.05–3.23(br,4H), 3.45–3.75(br,4H), 4.02–4.31(m,3H), 5.10 (s,3H), 6.80–7.50(m,15H).

EXAMPLE X

O-(N-Methyl)-Carbamoyl-D-Phenylalaninol Hydrochloric Acid Salt

In a 500 mL Parr reactor, O-(N-methyl)-carbonyl-N-benzyloxycarbonyl-D-phenylalaninol (2.80 g) obtained in Example I was dissolved in 80 mL of anhydrous methanol and added with palladium(carbon powder 10%, 0.10 g). Then, the reactor was closed and purged with hydrogen for 1 min. The reaction was completed in 7 hours under 50 psi hydrogen pressure at ambient temperatures, which was confirmed on thin layer chromatography. The catalyst was filtered off. Thereafter, the organic layer thus obtained was concentrated through distillation into 1.43 g (84%) of pale yellow liquid. The liquid was poured in 30 mL of anhydrous THF and cooled to 0° C. Anhydrous hydrochloric acid was then added, to give a desirable white precipitate. Addition of 30 mL of anhydrous ether maximized the precipitation. Filtration provided 1.36 g of the title compound as a white solid: Yield 68%.

Melting point=162°–163° C.

$^1$H-NMR(DMSO-D6, 200 MHz), ppm(δ): 2.28–3.18(m, 5H), 3.48–3.75(br,1H), 3.80–4.22(m,2H), 6.98–7.65(m,6H), 8.45(br,3H).

EXAMPLE XI

O-(N-Isopropyl)-Carbamoyl-D-Phenylalaninol Hydrochloric Acid Salt

The title compound was prepared in a similar manner to that of Example X, except that O-(N-isopropyl)-carbamoyl-N-benzyloxycarbonyl-D-phenylalaninol was used as the starting material.

Melting Point: 170°–171° C.

$^1$H-NMR(DMSO-D6, 200 MHz), ppm(δ): 1.08(d,6H), 2.82–3.18(m,2H), 3.48–3.75(m,2H), 3.85–4.15(m,2H), 7.15 (s,1H), 7.22–7.45(m,5H), 8.45(br,3H).

EXAMPLE XII

O-(N-Octyl)-Carbamoyl-D-Phenylalaninol Hydrochloric Acid Salt

The title compound was prepared in a similar manner to that of Example X, except that O-(N-octyl)-carbamoyl-N-benzyloxycarbonyl-D-phenylalaninol was used as the starting material.

Melting Point: 105°–106° C.

$^1$H-NMR(DMSO-d6, 200 MHz), ppm(δ): 1.08(t,3H), 1.18–1.55(m,12H), 2.78–3.16(m,4H), 3.62(br,1H), 3.82–4.15(m,2H), 7.15(t,1H), 7.25–7.45(m,5H), 8.35(br, 3H).

EXAMPLE XIII

O-(N-Cyclohexyl)-Carbamoyl-D-Phenylalaninol Hydrochloric Acid Salt

The title compound was prepared in a similar manner to that of Example X, except that O-(N-cyclohexyl)-carbamoyl-N-benzyloxycarbonyl-D-phenylalaninol was used as the starting material.

Melting Point: 232°–233° C.

$^1$H-NMR(DMSO-d6, 200 MHz), ppm(δ): 0.98–1.88(m, 10H), 2.78–3.16(m,2H), 3.25(br,1H), 3.65(br,1H), 3.82–4.12(m,2H), 7.15(d,1H), 7.22–7.45(m,5H), 8.35(br, 1H).

EXAMPLE XIV

O-(N,N'-Dimethyl)-Carbamoyl-D-Phenylalaninol Hydrochloric Acid Salt

The title compound was prepared in a similar manner to that of Example X, except that O-(N,N'-dimethyl)-carbamoyl-N-benzyloxycarbonyl-D-phenylalaninol was used as the starting material.

Melting Point: 129°–130° C.

$^1$H-NMR(DMSO-d6, 200 MHz), ppm(δ): 2.65–2.99(m, 6H), 2.99–4.16(m,5H), 7.05–7.45(m,5H), 8.48(br,3H).

EXAMPLE XV

O-(N-Pyrrolidyl)-Carbamoyl-D-Phenylalaninol Hydrochloric Acid Salt

The title compound was prepared in a similar manner to that of Example X, except that O-(N-pyrrolidyl)-carbamoyl-N-benzyloxycarbonyl-D-phenylalaninol was used as the starting material.

Melting Point: 224°–225° C.

$^1$H-NMR(DMSO-d6, 200 MHz), ppm(δ): 1.52–1.98(m, 4H), 2.72–3.76(m,7H), 3.78–4.22(m,2H), 7.02–7.52(m,5H), 8.58(br,3H).

EXAMPLE XVI

O-(N-Piperidyl)-Carbamoyl-D-Phenylalaninol Hydrochloric Acid Salt

The title compound was prepared in a similar manner to that of Example X, except that O-(N-piperidyl)-carbamoyl-N-benzyloxycarbonyll-D-phenylalaninol was used as the starting material.

Melting Point: 190°–191° C.

$^1$H-NMR(DMSO-d6, 200 MHz), ppm($\delta$): 1.18–1.72(m, 6H), 2.68–3.76(m,7H), 3.78–4.22(m,2H), 7.02–7.52(m,5H), 8.58(br,3H).

EXAMPLE XVII

O-(N-Morpholino)-Carbamoyl-D-Phenylalaninol Hydrochloric Acid Salt

The title compound was prepared in a similar manner to that of Example X, except that O-(N-morpholino)-carbamoyl-N-benzyloxycarbonyl-D-phenylalaninol was used as the starting material.

Melting Point: 207°–208° C.

$^1$H-NMR(DMSO-d6, 200 MHz), ppm($\delta$): 2.76–3.25(m, 2H), 3.25–3.82(m,9H), 3.86–4.22(m,2H), 7.12–7.52(m,5H), 8.48(br,3H).

EXAMPLE XVIII

O-[N-(N-Phenyl)piperazino]-Carbamoyl-D-Phenylalaninol Hydrochloric Acid Salt The title compound was prepared in a similar manner to that of Example X, except that O-[N-(N-phenyl)piperazino]-carbamoyl-N-benzyloxycarbonyl-D-phenylalaninol was used as the starting material.

Melting Point: 241°–242° C.

$^1$H-NMR(CDCl$_3$, 200 MHz), ppm($\delta$): 2.76–4.32(m,13H), 6.98–7.82(m,10H), 8.72(br,3H).

As described hereinbefore, the compounds represented by Structural Formula I were observed to be useful for the prophylaxis and treatment of CNS disorder including pain, depression, anxiety, epilepsy, stroke, demential and Parkinson's disease.

The present invention has been described in an illustrative manner, and it is to be understood that the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. An O-carbamoyl-(D)-phenylalaninol compound, represented by the following structural formula V:

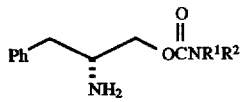

wherein $R^1$ and $R^2$ may be the same as or different from each other and are independently selected from the group consisting of hydrogen and lower alkyl containing 1 to 8 carbon atoms, and wherein $R^1$ and $R^2$ may be joined to form a 5 to 7-membered aliphatic cyclic radical which may comprise 0 to 1 additional nitrogen or 0 to 1 oxygen atoms directly unconnected, and the pharmaceutically acceptable salts thereof.

2. The compound in accordance with claim 1, wherein O-carbamoyl-(D)-phenylalaninol of the structural formula V comprises the compounds having the following general formulas:

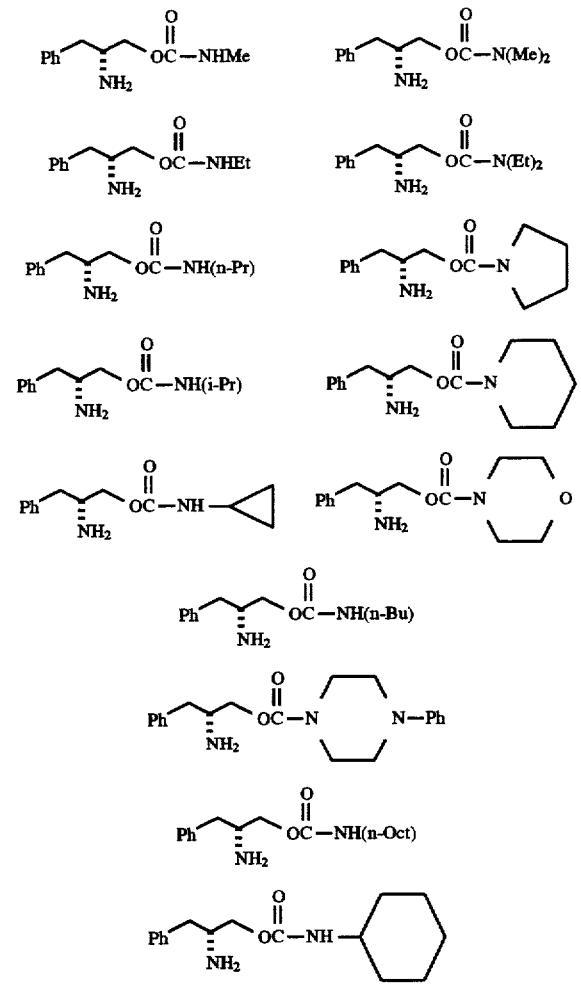

* * * * *

(12) REEXAMINATION CERTIFICATE (4292nd)
United States Patent
Choi et al.

(10) Number: US 5,705,640 C1
(45) Certificate Issued: Mar. 20, 2001

(54) O-CARBAMOYL-(D)-PHENYLALANINOL COMPOUNDS, THEIR PHARMACEUTICALLY USEFUL SALTS AND PROCESS FOR PREPARING THE SAME

(75) Inventors: Yong Moon Choi, Towaco, NJ (US); Dong Il Han; Yong Kil Kim, both of Taejon (KR)

(73) Assignee: SK Corporation, Fairfield, NJ (US)

Reexamination Request:
No. 90/005,500, Sep. 22, 1999

Reexamination Certificate for:
Patent No.: 5,705,640
Issued: Jan. 6, 1998
Appl. No.: 08/596,496
Filed: Feb. 5, 1996

(30) Foreign Application Priority Data

Feb. 11, 1995 (KR) .................................. 1995-2543

(51) Int. Cl.$^7$ ................................. C07D 265/30
(52) U.S. Cl. .................. 544/169; 544/389; 546/226; 548/531; 560/115; 560/163
(58) Field of Search ..................... 544/169, 389; 546/226; 548/531; 560/115, 163

(56) References Cited

FOREIGN PATENT DOCUMENTS 1434826  5/1976  (GB).

*Primary Examiner*—Michael L. Shippen

(57) ABSTRACT

The present invention relates to O-carbamoyl-(D)-phenylalaninol compound represented by the following structural formula V and pharmaceutically acceptable salts thereof to treat diseases of the central nervous system:

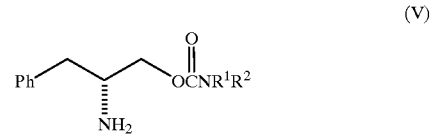

(V)

wherein $R^1$ and $R^2$ may be the same with or different from each other and are independently selected from the group consisting of hydrogen, lower alkyl containing 1 to 8 carbon atoms, and 5 to 7-membered aliphatic cyclic compounds which may comprise not more than two nitrogen or oxygen atoms directly unconnected, the total number of carbon atom of $R^1$ and $R^2$ ranging from 0 to 16.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1 and 2 is confirmed.

* * * * *